United States Patent [19]

Richmond et al.

[11] 3,955,567
[45] May 11, 1976

[54] BONE BRACE
[75] Inventors: James W. Richmond, Comstock Township, Kalamazoo County; Jeffrey S. Topf, Huntington Woods, both of Mich.
[73] Assignee: Stryker Corporation, Kalamazoo, Mich.
[22] Filed: Nov. 8, 1974
[21] Appl. No.: 522,024

[52] U.S. Cl. .............................. 128/92 D; 32/10 A; 128/89 A
[51] Int. Cl.² .......................................... A61F 5/04
[58] Field of Search ........ 32/10 A; 128/92 D, 89 A, 128/92 R, 92 B, 92 C, 89

[56] References Cited
UNITED STATES PATENTS

| | | | |
|---|---|---|---|
| 2,133,859 | 10/1938 | Hawley | 128/92 D |
| 2,362,741 | 11/1944 | Berke | 128/89 A |
| 3,593,709 | 7/1971 | Halloran | 128/92 D |

Primary Examiner—Louis G. Mancene
Assistant Examiner—Jack Q. Lever
Attorney, Agent, or Firm—Woodhams, Blanchard and Flynn

[57] ABSTRACT

A three dimensional implantable bone brace having a pair of elongated integral flanges connected along one lengthwise edge of each and disposed substantially at right angles to each other. One of said flanges has a plurality of spaced transverse slots which permit bending of the other flange in a direction parallel with said one flange. The other flange has a plurality of openings through which screw means can be inserted for fixing said brace against the lateral surface of a mandible, for example, when said one flange extends into a groove cut into said surface.

3 Claims, 5 Drawing Figures

BONE BRACE

BACKGROUND OF THE INVENTION

This invention relates in general to a three dimensional, implantable bone brace and, more particularly, to a type thereof capable of being readily adapted to repair a fractured mandible or to bridge and maintain the spacing between portions of an avulsed or resected mandible or to hold a bone graft with respect to a mandible.

With existing types of implantable bone plates or jaw pinning or wiring techniques, it is frequently necessary to immobilize the jaw for prolonged periods during which the healing is taking place. As the result, particularly where the patient has had sufficient trauma to the tempromandibular joint with a resultant hemarthrosis, immobilization of the mandible for prolonged periods may develop post-operative ankylosis of this joint. In addition to the discomfort and inconvenience experienced by the patient, the immobilization invites post-operative airway embarrassment, disrupts the normal intake of food, and offers a serious problem in treating the mentally deficient, the epileptic, the uncooperative and the unconscious patient.

The use of implantable bone plates is well known and, in fact, includes the use of three-dimensional bone braces. However, existing bone plates or braces are not readily adaptable to use on curved surfaces while, at the same time, providing sufficient rigidity for such curved surface, as is found on the lateral surface of the mandible. Thus, even with the use of implantable bone plates of an existing type, it has often been necessary to immobilize the jaw or mandible. On the other hand, three-dimensional bone plates having the inherent rigidity capable of fixing together the fractured or avulsed parts of the mandible have not been readily capable of deformation for the purpose of conforming to the shape of the mandible.

Accordingly, a primary object of the invention has been the provision of a three-dimensional bone plate or brace having sufficient rigidity to serve as an implantable brace attachable to the mandible to hold firmly together parts on opposite sides of a fracture line, or parts thereof on opposite sides of a zone in the mandible which has been avulsed or resected or to hold a bone graft in place.

A further object of this invention has been the provision of a bone brace, as aforesaid, in which the conforming of the brace can be readily accomplished by the physician at the time the brace is being implanted.

A further object of the invention is the provision of a bone brace, as aforesaid, which, after healing has completed, creates a minimum of disfigurement in the appearance of the patient due to the presence of the implant.

Other objects and purposes of the invention will become apparent to persons familiar with surgical implants and the like upon reading the following specification and examining the accompanying drawings in which.

Figure 1:
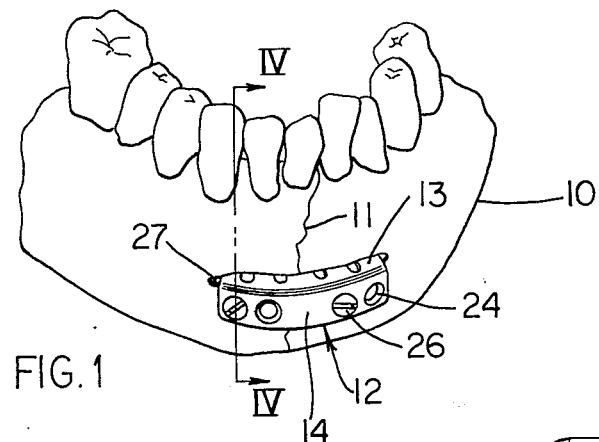
FIG. 1 is a fragmentary showing of a mandible having a three-dimensional bone brace secured thereto according to the teachings of the ivention.

For convenience in description, the terms "upper", "lower" and words of similar import shall have reference to the bone brace of the invention as appearing in FIG. 1. The terms "inner", "outer" and words of similar import will have reference to the bone brace as appearing in FIG. 2 wherein the inner side thereof is shown.

GENERAL DESCRIPTION

The objects and purposes of this invention have been met by providing a three-dimensional implantable bone brace comprised of an elongated angle member having a pair of elongated flanges with adjoining edges, said flanges being substantially perpendicular to each other. One of said flanges is provided with a plurality of spaced slots which extent from adjacent the inner surface of the other flange through the free edge of the said one flange, thereby permitting said other flange to be bent into a substantially arcuate shape. The one flange is inserted into a groove cut into the lateral surface of the mandible, and said other flange extends downwardly snugly adjacent the mandible so that it can be affixed thereto by screws which extend through appropriate openings in said other flange and thence into the mandible.

DETAILED DESCRIPTION

FIG. 1, which illustrates a preferred embodiment of the invention and its use, shows a fractured fragment of the front end of a mandible 10, the fracture being shown by the line 11. The three-dimensional bone brace 12, mounted on the mandible 10, has an upper flange 13 (FIGS. 2 and 3) and lower flange 14 which are elongated. The flanges are integrally connected along a pair of lengthwise edges defined by the junction line 15 therebetween. The flanges 13 and 14 are substantially rectangular and are positioned substantially perpendicularly to each other. The free edges 17 and 18 of the flanges 13 and 14, respectively, are preferably straight, parallel and spaced approximately the same distance from the junction line 15, when the brace 12 is in its initial shape.

The upper flange 13 has a plurality of transverse, uniformly spaced slots 19 which extend from adjacent the inner surface of the lower flange 14 through the free edge 17 of said upper flange. In the preferred embodiment of the invention, the interior ends 22 of the slots 19 are rounded, but could be pointed or flat. The separated portions 23 of the upper flange 13 are preferably in the range of approximately 0.050 to 0.090 of an inch apart and, in a direction lengthwise of said flange 13, said portions 23 are in the range of approximately 0.100 to 0.140 of an inch long.

The flanges 13 and 14 are preferably of substantially the same thickness which is in the range of approximately 0.030 to 0.050 of an inch. The widths of said flanges are in the range of approximately 0.200 to 0.250 of an inch.

The foregoing dimensions depend upon the specific location of usage, the size of the mandible and the extent of the injury or damage being repaired. For example, the aforesaid dimensions, which are designed for an adult or young adult, might be advantageously reduced substantially for use on a small child. The length of the brace may vary considerably, again depending upon the extent and nature of the damage being repaired, but is usually in the range of from 25 mm. to 60 mm.

Figure 2:
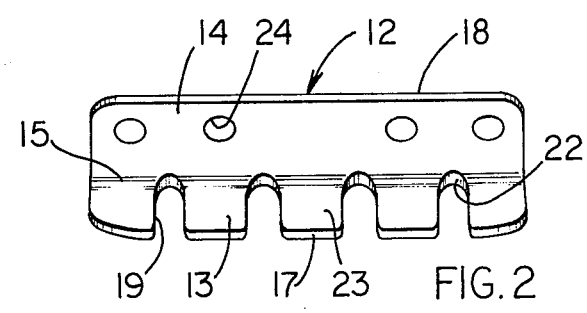
FIG. 2 is a side elevational view of said bone brace.
Figure 3:
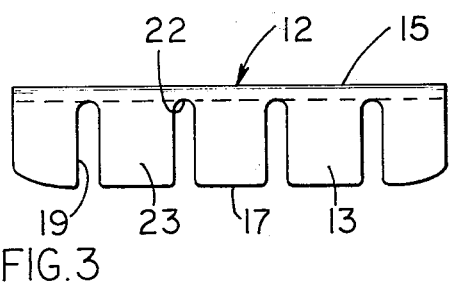
FIG. 3 is a top plan view of said bone brace.
Figure 5:
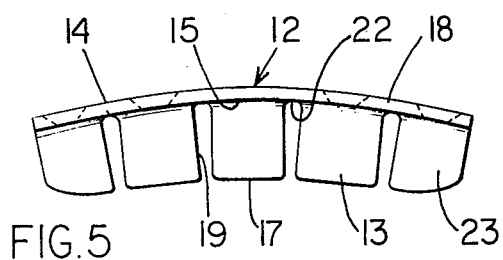
FIG. 5 is a bottom view of said brace shown in an arcuate form just prior to application thereof to the patient.

The bone brace 10 is normally furnished to the doctor in the form appearing in FIGS. 2 and 3. The material of the brace, which may be a special stainless steel, silver, gold or platinum, for example, is sufficiently rigid to give adequate support to the fractured or grafted mandible. Said metal is also sufficiently bendable that the doctor can shape it into a substantially arcuate form, as appearing in FIG. 5, such form corresponding to the lateral surface of the mandible to which the brace will be applied.

If stainless steel is used in the brace implant, it must conform to the formulation specified by the American Society for Testing and Materials which is identified as ASTM F-56-66. This formulation sets specific percentage maximums for carbon, manganese, phosphorus, sulphur and silicone. It also specifies ranges for the nickel, molybdenum and chromium contents.

Figure 4:
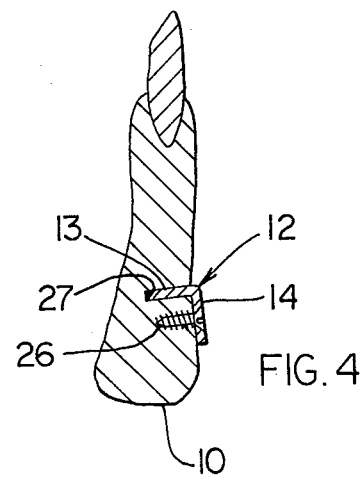
FIG. 4 is a sectional view substantially as taken along the line IV—IV in FIG. 1.

The lower flange 14 has a plurality of screw openings 24 therethrough (FIG. 1) whereby screws 26 (FIGS. 1 and 4) can be inserted through said lower flange and thence into the mandible after the upper flange has been inserted into a groove 27 in the mandible. After securement of the brace 12 in place, the surgical procedures can be completed by closing the wound in the usual manner. While post-operative care must obviously be exercised in the use and movement of the mandible until the fracture can mend, the patient will be able to move his jaw in most instances fairly normally for the purpose of talking and receiving nourishment. Such movement also avoids weakening of the lower jaw muscles and a stiffening of the jaw's hinge joint which must be cured subsequently. In other words, the brace of the invention permits and provides for a process of bracing and healing of a fractured mandible not previously available.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A three-dimensional bone brace for securement to an injured mandible having a groove cut in the lateral surface thereof, comprising:

an elongated L-shaped metallic angle member having first and second substantially rectangular flanges disposed substantially at right angles to each other, each of said flanges having a free edge extending longitudinally of said angle member, the free edges of said flanges being substantially parallel;

means for permitting said first flange to be bent into a substantially arcuate and nonplanar shape conforming to the lateral surface of the mandible when a material bending force is applied to said angle member, said means comprising a plurality of substantially uniformly spaced slots in said second flange, each slot extending transversely of said second flange from a point substantially adjacent the inner surface of the first flange through the free edge of said second flange, said slots permitting bending of said second flange within the plane thereof; and a plurality of openings extending through said first flange for reception of screw means whereby said first flange can be fixedly secured snugly against the lateral surface when the second flange is disposed within a said groove in said mandible, said openings being spaced inwardly from the free edge of said first flange, and the free edge of said first flange being substantially straight and continuous throughout the length of said angle member.

2. A bone brace according to claim 1 wherein each of said slots is elongated in a direction extending transversely across said second flange, each of said slots being of narrow and substantially uniform width throughout the length thereof, whereby said slots divide said second flange into a plurality of substantially rectangular separated portions which project transversely from said first flange in a cantilevered manner.

3. A bone brace according to claim 2, wherein adjacent ones of said rectangular portions have opposed edges defining one of said slots therebetween, said opposed edges being substantially parallel and spaced apart by a distance in the range of between about 0.050 and 0.090 of an inch.

* * * * *